United States Patent
Ulrich et al.

(10) Patent No.: US 11,002,643 B1
(45) Date of Patent: May 11, 2021

(54) IN-SITU DEVICE FOR COLLECTING MINERALS

(71) Applicant: Arcadis U.S., Inc., Highlands Ranch, CO (US)

(72) Inventors: Shannon Ulrich, Broomfield, CO (US); Jennifer P. Tilton, Raleigh, NC (US); Jeffery P. Ford, Raleigh, NC (US); David Liles, Durham, NC (US); Craig Divine, Irvine, CA (US); Shandra Justica-Leon, Guaynabo, PR (US); Jeff Gillow, Denver, CO (US)

(73) Assignee: ARCADIS U.S., INC, Highlands Ranch, CO (US)

(*) Notice: Subject to any disclaimer, the term of this patent is extended or adjusted under 35 U.S.C. 154(b) by 176 days.

(21) Appl. No.: 16/180,443

(22) Filed: Nov. 5, 2018

Related U.S. Application Data

(60) Provisional application No. 62/720,765, filed on Aug. 21, 2018.

(51) Int. Cl.
  *G01N 1/10* (2006.01)
  *E21B 43/08* (2006.01)
  *G01N 33/18* (2006.01)

(52) U.S. Cl.
  CPC .............. *G01N 1/10* (2013.01); *E21B 43/082* (2013.01); *E21B 43/084* (2013.01); *G01N 33/1853* (2013.01)

(58) Field of Classification Search
  CPC ........ E21B 43/08–088; G01N 33/1853; G01N 1/10; G01N 2001/149
  See application file for complete search history.

(56) References Cited

U.S. PATENT DOCUMENTS

| | | | | |
|---|---|---|---|---|
| 4,366,054 A | * | 12/1982 | Kronsbein | ......... B01D 39/2058 210/266 |
| 8,197,687 B2 | * | 6/2012 | Krogue | ................... C02F 1/281 210/282 |

OTHER PUBLICATIONS

Dong. Integration of nanoscale zero-valent iron and functional anaerobic bacteria for groundwater remediation: A review. (2019). 13 pages.
Dong. The Relative Contributions of Abiotic and Microbial Processes to the Transformation of Tetrachloroethylene and Trichloroethylene in Anaerobic Microcosms. 2009.
Zhang. Autotrophic Vanadium(V) Bioreduction in Groundwater by Elemental Sulfur and Zerovalent Iron. 2018. 9 pages.
Geochemical and Isotope Study of Trichloroethene Degradation in a Zero-Valent Iron Permeable Reactive Barrier: A Twenty-Two-Year Performance Evaluation. 11vpages.
Schaefer, C.E., Ho, P.H., Berns, E., Werth, C. (2018) Mechanisms for Abiotic Dechlorination of Trichloroethene by Ferrous Minerals under Oxic and Anoxic Conditions in Natural Sediments. Environmental Science and Technology, 52:13747-13755. 9 pages.
Workshop on In Situ Biogeochemical Transformation of Chlorinated Solvents. 2008. 66 pages.

(Continued)

*Primary Examiner* — Justin N Olamit
(74) *Attorney, Agent, or Firm* — Lewis Brisbois Bisgaard and Smith, LLP

(57) ABSTRACT

An in-situ monitoring tool is provided that is compromised of a non-reactive medium, a reactive medium, or a combination thereof, contained in a water-permeable mesh. The tool is placed in an aquifer for a predetermined amount of time to allow the medium(s) to act as a substrate that collects minerals from the aquifer for analysis.

7 Claims, 5 Drawing Sheets

(56) References Cited

OTHER PUBLICATIONS

Amonette. Dechlorination of Crbc9 Tetrachloride by Fe(II) Associated with Goetri. 8 pages.
Magnetic Susceptibility—Magnetite. 2 pages.
Barajas-Rodrigueza. Aerobic biodegradation kinetics for 1,4-dioxane under metabolic and cometabolic conditions. 2018. 9 pages.
Bethke. The Thermodynamic Ladder in Geomicrobiology. 2011. 28 pages.
Biologically Mediated Degradation of Chlorinated Ethenes: A New Conceptual Framework. 2018. 2 pages.
Bourdoiseau, J.-A., Jeannin, M., Sabot, R., Remazeilles, C., Refait, Ph. (2008) Characterization of mackinawite by Raman spectroscopy: Effects of crystallization, drying and oxidation. Corrosion Science, 50, 3247-3255. 9 pages.
Boursiquot, S., Mullet, M., Abdelmoula, M., Genin, J.-M. (2001) the dry oxidation of tetragonal FeS1-x mackinawite. Physics and Chemistry of Minerals, 28, 600-611.
Bowen. Design and Testing of a Convenient Benchtop Sandbox for Controlled Flow Experiments. 2012. 5 pages.
Brown. Monitored Natural Attenuation Forum: The Case for Abiotic MNA. 2007. 11 pages.
Brown. Interactions Between Biological and Abiotic Pathways in the Reduction of Chlorinated Solvents. 2009. 12 pages.
Bulter. Kinetics of the Transformation of Trichloroethylene and Tetrachloroethylene by Iron Sulfide. 1999. 7 pages.
Butler. Factors Influencing Rates and Products in the Transformation of Trichloroethylene by Iron Sulfide and Iron Metal. 2001. 9 pages.
Bulter. Transformation of Trichloroethylene to Predominantly Non-Regulated Products under Stimulated Sulfate Reducing Conditions. 2013. 22 pages.
Chen. Two-stage chromium isotope fractionation during microbial Cr(VI) reduction. 2018. page 9.
Culpepper. Reduction of PCE and TCE by magnetite revisited. 2018. 23 pages.
He et al. Identification and characterization methods for reactive minerals responsible for natural attenuation of chlorinated organic compounds in ground water, EPA600-R09/115/. USEPA (2009). 152 pages.
He, Y.T., Wilson, J.T., Su, C., Wilkin, R.T. (2015) Review of abiotic degradation of chlorinated solvents by reactive iron minerals in aquifers. Groundwater Monitoring & Remediation. 35:57-75.
He. Impact of iron sulfide transformation on trichloroethylene degradation. 2010. 15 pages.
He. Transformation of Reactive Iron Minerals in a Permeable Reactive Barrier (Biowall) Used to Treat TCE in Groundwater. 2018. 18 pages.
Darlington. Biotic and Abiotic Anaerobic Transformations of Trichloroethene and cis-1,2-Dichloroethene in Fractured Sandstone. 2008.
Davis. Addition of divalent iron to electron donor mixtures for remediation of chlorinated ethenes: A study of 100 wells. 2018.
Devlin. Field and Laboratory Studies of Carbon Tetrachloride Transformation in a Sandy Aquifer under Sulfate Reducing Conditions. 1999.
Elsner. Reactivity of Fe(II)-Bearing Minerals toward Reductive Transformation of Organic Contaminants. 2004.
Scherer. Biologically Mediated Abiotic Degradation of Chlorinated Ethenes: A New Conceptual Framework. 2015.
Scherer. Fe(II)—Fe(III) electron transfer in Fe oxides and clays: Implications for contaminant transformations. 2010.
Vikesland. Particle Size and Aggregation Effects on Magnetite Reactivity toward Carbon Tetrachloride.2007.
Ferrey. Nonbiological Removal of cis-Dichloroethylene and 1,1-Dichloroethylene in Aquifer Sediment Containing Magnetite. 2004.

Kennedy, L.G., Everett, J., 2004. Final Report: Field Test of Biogeochemical Reductive Dechlorination at Dover Air Force Base Dover, Deleware. Air Force Center for Environmental Excellence, Dec. 2004.
Mills, J.C.; Wilson, J.T.; Wilson, B.H.; Wiedemeier, T.H.; Freedman, D.L. (2018) Quantification of TCE co-oxidation in groundwater using a 14C-assay. Groundwater Monitoring & Remediation 38(2), 57-67.
Kennedy. Assessment of biogeochemical natural attenuation and treatment of chlorinated solvents, Altus Air Force Base, Altus, Oklahoma. 2006.
Jeong. Abiotic Reductive Dechlorination of cis-Dichloroethylene by Fe Species Formed during Iron- or Sulfate-Reduction. 2011.
Jeong. Reductive Dechlorination of Tetrachloroethylene and Trichloroethylene by Mackinawite (FeS) in the Presence of Metals: Reaction Rates. 2007.
Freedman. Biological Reductive Dechlorination of Tetrachloroethylene and Trichloroethylene to Ethylene under Methanogenic Conditions. 1989.
Fullerton. Anaerobic Oxidation of Ethene Coupled to Sulfate Reduction in Microcosms and Enrichment Cultures. 2013.
Hanoch. Transformation of carbon tetrachloride by bisulfide treated goethite, hematite, magnetite, and kaolinite. 2005.
Yu, R., Andrachek, R.G., Lehmicke, L.G., Freedman, D.L. (2018) Remediation of chlorinated ethenes in fractured sandstone by natural and enhanced biotic and abiotic processes: A crushed rock microcosm study. Science of the Total Environment. 626:497-506.
Weidemeier, T.H., Wilson, B.H., Ferry, M.L., Wilson, J.T. (2017) Efficacy of an in-well sonde to determine magnetic susceptibility of aquifer sediment. Groundwater Monitoring & Remediation. 37(2): 25-34.
Air Force Center for Engineering and the Environment (2008). Technical protocol for enhanced anaerobic bioremediation using permeable mulch biowalls and bioreactors. Prepared by Parsons Infrastructure & Technology Group, Inc., Denver, Colorado. Final, May 2008. 302 pages.
Mehta, V.S., F. Maillot, Z. Wang, J.G. Catalano, and D.E. Giammar. 2016. Effect of Reaction Pathway on the Extent and Mechanism of Uranium(VI) Immobilization with Calcium and Phosphate. Environmental Science and Technology, 50, 3128-3136. 9 pages.
Whiting, K., Evans, P.J. Lebron, C., Henry, B., Wilson, J.T., and E. Becvar (2014). Factors controlling in-situ biogeochemical transformation of trichloroethene: field study. Groundwater Monitoring & Remediation. 34: 79-94.
Haas. Halocarbons in the environment: Estimates of thermodynamic properties for aqueous chloroethylene species and their stabilities in natural settings. 1999.
Hansson. Influence of Na2S on the degradation kinetics of CCl4 in the presence of very pure iron. 2008.
Huo. Biogenic FeS accelerates reductive dechlorination of carbon tetrachloride by Shewanella putrefaciens CN32. 2016.
Hyun. Feasibility of Using In Situ FeS Precipitation for TCE Degradation. 2009.
Kenneke. Reductive Dehalogenation of Halomethanes in Iron- and Sulfate-Reducing Sediments. 1. Reactivity Pattern Analysis. 2003.
Larese-Casanovaand. Fe(II) Sorption on Hematite: New Insights Based on Spectroscopic Measurements. 2007.
Lee. Iron hydroxy carbonate formation in zerovalent iron permeable reactive barriers: Characterization and evaluation of phase stability. 2010.
McCormick. Carbon Tetrachloride Transformation on the Surface of Nanoscale Biogenic Magnetite Particles. 2004.
Mueller. Design and Selection Criteria for Implementing ISCR Technologies.
O'Loughlin. Effects of Oxyanions, Natural Organic Matter, and Bacterial Cell Numbers on the Bioreduction of Lepidocrocite (γFeOOH) and the Formation of Secondary Mineralization Products. 2010.
Pedersen. Fast transformation of iron oxyhydroxides by the catalytic action of aqueous Fe(II). 2005.
Pham. Trichloroethylene Transformation by Natural Mineral Pyrite: The Deciding Role of Oxygen. 2008.

(56) References Cited

OTHER PUBLICATIONS

Wilkin, R.T. Mineralogical preservation of solid samples collected from anoxic subsurface environments. EPA/600/R-06/112. (2006). 8 pages.
Rickard. Kinetics of pyrite formation by the H2S oxidation of iron (II) monosulfide in aqueous solutions between 25 and 125° C.: The rate equation. 1997.
Su. Travel distance and transformation of injected emulsified zerovalent iron nanoparticles in the subsurface during two and half years. 2013.
Rugge. Characterization of Predominant Reductants in an Anaerobic Leachate-Contaminated Aquifer by Nitroaromatic Probe Compounds. 1998.
Weerasooriya. Pyrite-assisted degradation of trichloroethene (TCE). 2001.
Tobiszewski. Abiotic degradation of chlorinated ethanes and ethenes in water. 2012.
Trolard. Identification of a green rust mineral in a reductomorphic soil by Mossbauer and Raman spectroscopies. 1997.
Tang. Magnetic nanoparticles: Essential factors for sustainable environmental applications. 2013.
Shao. Influence of Soil Minerals on the Rates and Products of Abiotic Transformation of Carbon Tetrachloride in Anaerobic Soils and Sediments. 2008.
Wilkin. Nickel sulfide formation at low temperature: initial precipitates, solubility and transformation products. 2010.
Wilkin. Uptake of nickel by synthetic mackinawite. 2017.
Baldwin, B.R., Peacock, A.D., Ying-Dong, M.G., Resch, C.T., Arntzen, E., Smithgall, A.N., Pfiffner, S.M., Frefield, B.M., White, D.C., Long, P.E. (2009) In-well sediment incubators to evaluate microbial community stability and dynamics following bioimmobilization of uranium. Remediation. 19:73-89.
Busch-Harris, J., Sublette, K.L., Roberts, K.P., Landrum, C., Peacock, A.D., Davis, G., Ogles, D., Holmes, W.E., Harris, D., Ota, C., Yang, X., Kolhatkar, A. (2008) Bio-Traps Coupled with Molecular Biological Methods and Stable Isotope Probing Demonstrate the In Situ Biodegradation Potential of MTBE and TBA in Gasoline-Contaminated Aquifers. Groundwater Monitoring and Remediation 28:47-62.
ESTCP. (2015) Development and Validation of a Quantitative Framework and Management Expectation Tool for the Selection of Bioremediation Approaches at Chlorinated Ethene Sites . Environmental Security Technology Certification Program (ESTCP) Final Report Project ER-201129. https://www.serdp-estcp.org/Program-Areas/Environmental-Restoration/Contaminated-Groundwater/Persistent-Contamination/ER-201129/ER-201129/(language)/eng-US.
SERDP and ESTCP. (2018) Summary Report: SERDP and ESTCP Workshop on Research and Development Needs for Chlorinated Solvents in Groundwater. Oct. 2018.
Wiedemeier, T.H., J.T. Wilson, D.L. Freedman, B. Lee. (2017) Providing additional support for monitored natural attenuation by including quantitative lines of evidence for abiotic degradation and co-metabolic oxidation of chlorinated ethylenes. ESTCP Final Report for ER-201584. https://serdp-estcp.org/Program-Areas/Environmental-Restoration/Contaminated-Groundwater/Persistent-Contamination/ER-201584/ER-201584.
Williams, N., Hyland, A., Mitchener, R., Sublette, K., Key, K.C., Davis, G., Ogles, D., Baldwin, B., Biernacki, A. (2013) Demonstrating the In-situ Biodegradation Potential of Phenol Using Bio-Sep® Bio-Traps® and Stable Isotope Probing. Remediation Journal. 23(1):7-22. DOI: 10.1002/rem.21335.
SERDP Workshop on Acoustic Detection and Classification of Munitions in the Underwater Environment. 2018. 70 pages.
3D printed mixed flow reactor for geochemical rate measurements; F. Marc Michel, et al; Applied Geochemistry 89; 2018; pp. 86-91.
Pyrite formation and mineral transformation pathways upon sulfidation of ferric hydroxides depend on mineral type and sulfide concentration; Stefan Peiffer, et al; Chemical Geoglogy; 400; vol. 44; 2015; pp. 44-55.
Silicates, Silicate Weathering, and Microbial Ecology; P.C. Bennett, et al; Geomicrobiology Journal; vol. 18; 2001; pp. 3-19.

\* cited by examiner

IN-SITU DEVICE FOR COLLECTING MINERALS

This application is a continuation of U.S. patent application Ser. No. 16/180,443 filed on Nov. 5, 2018 which claims benefit of U.S. Patent Application Ser. No. 62/720,765, filed Aug. 21, 2018, the entirety of which are both incorporated by reference herein.

FIELD OF THE INVENTION

Embodiments of the present invention generally relate to an in-situ monitoring device adapted for insertion into an aquifer, such as a well. The monitoring tool collects minerals from the aquifer that are later tested to ascertain water quality.

BACKGROUND OF THE INVENTION

The standard approach to characterizing minerals at a field site being remediated involves soil sampling at depth via drilling, which can be costly and technical challenging. For a site underlain by competent or fractured rock, these challenges are more significant. While confirmatory subsurface soil/rock sampling is a component of many remediation programs, extensive or repeated drilling events are often prohibitively expensive. Furthermore, data collected by these methods can be difficult to interpret due to the inherent variability and heterogeneity of geologic formations.

In addition, degradation of chlorinated methanes, ethanes, and ethenes via the reducing power stored in reactive minerals (e.g. iron sulfides, sorbed $Fe'$, green rust, etc.) is a subject of active research and cost-effective tools in support of field applications are needed. It has been documented that abiotic mechanisms, including the presence of reactive minerals, contribute to the overall treatment capacity within anaerobic biological treatment zones. This fraction of reactive minerals needed to substantially impact the overall degradation of chlorinated solvents is quite low—less than 0.5%. These biological and abiotic processes work synergistically, resulting in increasing in-situ degradation of chlorinated compounds. However, methods available to collect solid samples to characterize and quantify abiotic processes related to reactive minerals are limited, and all other evidence of these processes are indirect and usually comprised of water data or modeling.

In addition to the formation of reactive minerals for treatment of Chlorinated Volatile Organic Compounds (CVOCs), in-situ chemical oxidation (ISCO), and in-situ chemical reduction (ISCR) are common methods to remove trace metals from groundwater via oxidation or reduction and subsequent precipitation of the target contaminant (e.g., highly mobile arsenite to less mobile arsenate), and/or through oxidation and precipitation of iron which can remove trace metals through sorption and/or co-precipitation. Thus, there is a need for a monitoring device that can be installed in monitoring wells before or during treatment to demonstrate that treatments are working as designed. This includes virtually all situations where precipitation of a mineral is intended, such as arsenic removal via the precipitation of iron-arsenic compounds or uranium removal from groundwater using phosphate, a process which is currently being applied at commercial and federal sites across the United States.

Many in-situ groundwater treatment technologies used to address chlorinated solvents, as well as many other contaminants, rely upon the formation, dissolution, and/or transformation of target solid-phase minerals either to sequester or degrade groundwater contaminants. However, evaluation of these solid phase minerals and/or processes is often inferred from aqueous phase conditions, such as groundwater sampling because of the significant challenges and costs associated with solid phase sample collection. Traditionally, solid-phase samples include the use of high-cost drilling/coring techniques and sub-sampling of discrete zones within the core material for analysis. Again, these methods are costly and pose health and safety risks. Further, these methods obtain data from discrete points/depths within the subsurface, often requiring a relatively large sample number of wells to adequately characterize a subsurface area of interest as most possess high heterogeneity across very small areas.

SUMMARY OF THE INVENTION

It is one aspect of embodiment of the present invention to provide a device for monitoring the formation of target minerals in-situ, which is sometimes referred to as a "mineral trap." Mineral traps configured to collect minerals from an aquifer may be seamlessly integrated into a broad range of remediation programs in simple or complex geologic environments to provide more reliable data than current techniques at a low cost. Because of the cost savings, mineral traps can facilitate the increased utility of mineralogical data to support a broad range of technical and regulatory objectives at sites where traditional approaches to data are considered cost prohibitive. Mineral traps also represent an opportunity for significant cost savings at sites with complex and/or challenging geology. The contemplated mineral traps are also employed verify remediation processes and constrain treatment variables such as injection frequency, volume, and concentration by quickly providing indicators of subsurface treatment progress, efficiency, and long-term performance. Mineralogical data gathered from mineral traps could be applied to assess remedial objectives at several stages of the remedial program, including initial characterization, alternatives evaluation, feasibility testing, remedy optimization, and transition from active to passive treatment.

Virtually any in-situ remediation strategy that results either in the precipitation or dissolution of a solid-phase mineral species can be validated, monitored, or calibrated with the mineral traps of embodiments of the present invention. Mineral traps solve many challenges inherent to the field evaluation and deployment of remedial approaches that employ reactive minerals for contaminant destruction, i.e., in-situ biogeochemical or abiotic degradation. Mineral traps are also well suited in processes that are designed to precipitate contaminants and/or sequester contaminants into stable mineral forms, e.g., treating dissolved nickel by creating solid NiS minerals or treating dissolved uranium by incorporating it into phosphate minerals through the addition of phosphate into the aquifer. The contemplated mineral traps provide direct feedback from the subsurface regarding the presence and reactivity of relevant mineral phases. Additionally, costs, time, data quality concerns, and health and safety risks associated with drilling for mineral samples are avoided. Mineral traps provide a technical basis to support estimates of stored reactivity, which may suggest a transition from active to passive treatment. Finally, embodiments of the present invention allow for confirmation that passive treatment is being effective or following shutdown of active treatment, all issues continue to be resolved.

In addition to the formation of reactive minerals for treatment of CVOCs, In-Situ Chemical Oxidation (ISCO) is a common method to remove trace metals from groundwater either through the oxidation and subsequent precipitation of the target contaminant (e.g., highly mobile arsenite to less mobile arsenate), and/or through oxidation and precipitation of iron which can remove trace metals through sorption and/or co-precipitation. Low-cost mineral traps can be installed in monitoring wells before or during ISCO treatment and can conclusively demonstrate that the precipitation of iron-arsenic compounds, for example, is occurring. In another example, mineral traps can be applied to monitor uranium removal from groundwater using phosphate by providing a sample of the in-situ precipitated calcium-uranium-phosphate mineral. Mineral traps can also be used to conclusively show that the precipitated uranium-bearing phosphate mineral is stable and will not re-dissolve in groundwater.

Other applications of mineral traps may involve the dissolution of the tailored mineral compounds contained within the mineral traps itself. In an example of this application, a mixture of variably redox-sensitive iron minerals can be emplaced in the mineral traps during ISCR or Enhanced Reductive Dechlorination (ERD). Later examination of which mineral species dissolve and which persist can give an indication of the redox state of the system, which currently can only be estimated with a groundwater probe, and which only constitutes the redox state at one discrete point in time. This process can also help ascertain how this redox state could be affecting the minerals in the aquifer matrix. Many of the goals of ISCO, ISCR, and ERD are based on the precipitation of metals, so monitoring that process directly is essential to characterizing the effects of treatment. However, development of a high-quality data set to support these technical needs comes with the high costs and logistical challenges associated with the traditional drilling techniques described above. The highly versatile design of mineral traps allows users to tailor them to specific remedial needs. Given the large variety of contaminants and treatment approaches employed at Department of Defense (DoD) and other federal sites, as well as private industry sites, mineral traps provide a unique, versatile, and invaluable tool for directly monitoring and documenting treatment progress, especially to stakeholders and the public, at a fraction of the cost and risk associated with currently available approaches.

The contemplated mineral traps can also support remedy optimization by, for example, providing a basis for the transition from active treatment to a Monitored Natural Attenuation (MNA) approach. More specifically, data from mineral traps will provide a basis for ending active in-situ treatment and transitioning to MNA earlier, potentially saving hundreds of thousands of dollars per remediation site.

It is, thus another aspect of some embodiments to provide a mineral trap adapted to conclusively document natural mineralogic processes of interest occurring with the aquifer that support a successful MNA remedy. That is, the contemplated mineral traps can be used to document treatment longevity and support informed decisions on transitions from active remediation to passive technologies like MNA. One of ordinary skill in the art will appreciate that the mineral traps of the disclosed embodiment optimize long-term monitoring programs and support predictions of long-term effectiveness.

It is another aspect to provide a mineral trap that optimizes active treatment systems and refines treatment variables such as injection volume, concentration, and frequency by providing definitive evidence of subsurface treatment progress.

It is another aspect of some embodiments of the present invention to provide a method for correlating and calibrating reactive mineral formation within the mineral traps using co-located soil core samples collected using direct-push techniques.

The mineral trap technology described herein holds much promise for significantly improving the management of chlorinated solvent treatment by providing a reliable method for measuring reactive minerals in the subsurface, which is currently an unmet need. For chlorinated solvent sites, the formation of reactive minerals in-situ can be a prime line of evidence to evaluate the synergy between biological and abiotic processes.

For sites where metals treatment via precipitation is the correct remedy, such as the enhanced precipitation of hexavalent chromium, arsenic, nickel, or uranium, data collected from mineral traps provide direct confirmation that the target precipitation activity is occurring. Traditional approaches typically rely on a decline in aqueous contaminant concentrations, though the cause of the decrease is often unidentified as it can be attributed to dilution, change in groundwater flow paths, or precipitation as intended, etc. Mineral traps provide the opportunity to collect direct evidence using a monitoring well-based approach that can be more seamlessly integrated into existing groundwater monitoring programs. Mineral trap data can also be used to proactively evaluate the ongoing stability of mineral precipitates once formed without the need for repeated drilling events Mineral traps have the potential to significantly reduce the costs and health and safety risks for remedial programs where mineral formation, dissolution, or transformation is a component. Mineral traps also provide direct mineralogical data using the existing well network, which allows for an expanded set of sampling locations, repeated time series data, and the ability to evaluate consistent locations during modifications to the treatment program—without the need for repeated drilling events. In addition to improved data quality and significantly decreased costs compared to traditional drilling methods, the benefits of mineral traps also include decreased field hours, decreased health and safety risks, more efficient remedial operations, and improved communication with regulatory agencies. The DoD alone has many sites impacted with chlorinated solvents and/or metals, and a significant percentage of these sites are being addressed through in-situ technologies. Many of these sites could directly benefit from mineral traps to provide the data needed to optimize remedial performance while lowering costs and health and safety risks compared to drilling-based approaches.

Remediation strategies employing mineral traps are particularly suited to identify and quantify the formation of reactive iron minerals for the treatment of chlorinated compounds. The table provided below identifies potential technologies that could be monitored and validated using mineral traps.

| Process | Example Contaminant | Target Observation within the Mineral Traps |
|---|---|---|
| Enhanced Reductive Dechlorination | Chlorinated solvents | Reactive mineral formation, such as $FeS_x$ |

-continued

| Process | Example Contaminant | Target Observation within the Mineral Traps |
|---|---|---|
| In-situ Chemical Oxidation of metals | Arsenic, metals that form oxides | Iron oxides containing co-precipitated or adsorbed arsenic/other metalloids/metals |
| In-situ Chemical Reduction/ precipitation of metal sulfides | CrVI, U, metals that form sulfides | Increase in total chromium or uranium overtime, $FeS_x$ or other metal sulfide formation |
| pH Increase or Decrease | Metals | Increase in solid-phase metals |

The Summary of the Invention is neither intended nor should it be construed as being representative of the full extent and scope of the present invention. That is, these and other aspects and advantages will be apparent from the disclosure of the invention(s) described herein. Further, the above-described embodiments, aspects, objectives, and configurations are neither complete nor exhaustive. As will be appreciated, other embodiments of the invention are possible using, alone or in combination, one or more of the features set forth above or described below. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description given below, serve to explain the principles of these inventions.

Figure 1:
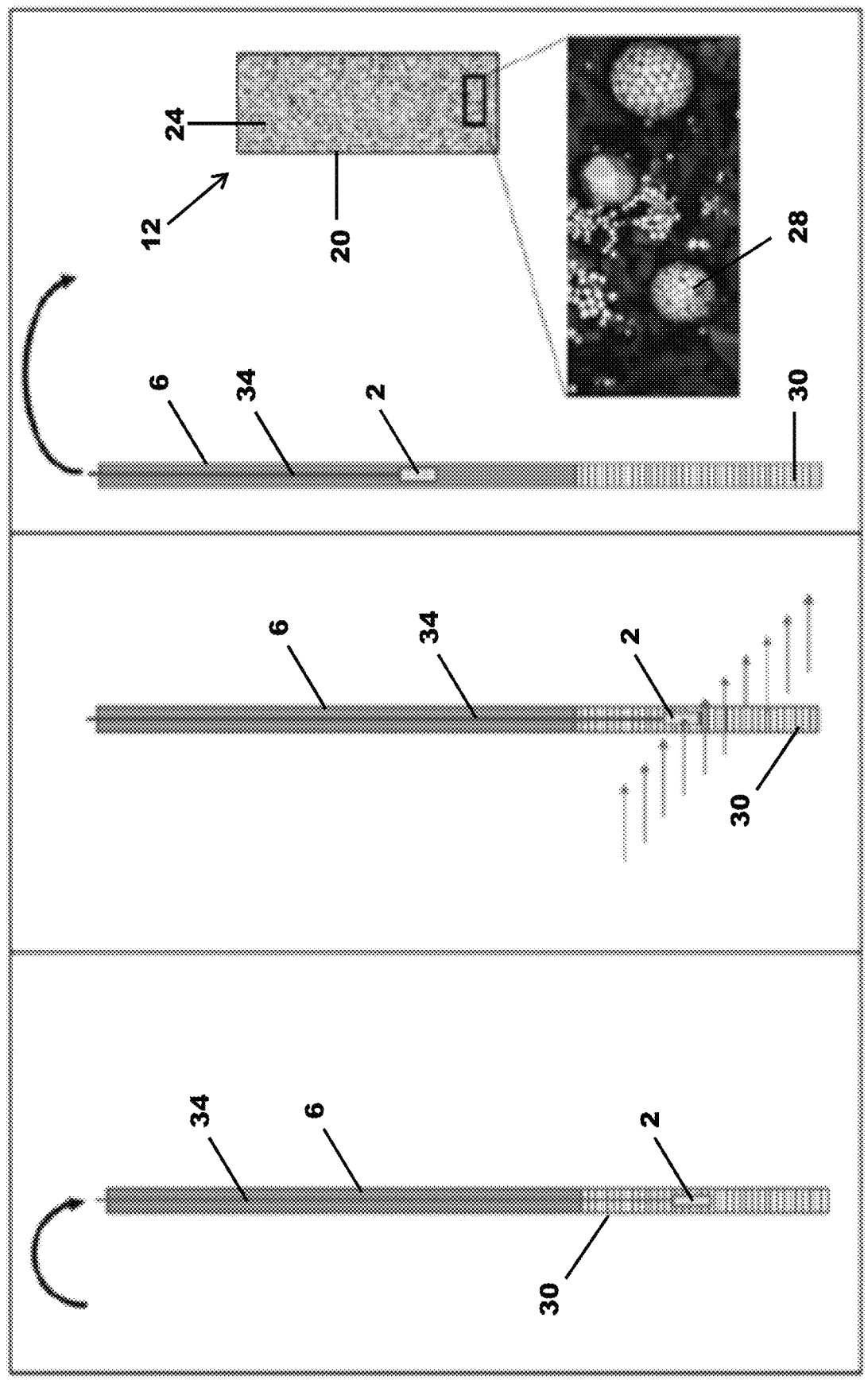
FIG. 1A is a schematic showing deployment of a mineral trap of one embodiment of the present invention into a well.
FIG. 1B is a schematic showing the mineral trap of FIG. 1A positioned in a well during an incubation phase.
FIG. 1C is a schematic showing the mineral trap shown in FIG. 1A being removed from a well for analysis.

The following component list and associated numbering found in the drawings is provided to assist in the understanding of one embodiment of the present invention:

| # | Component |
|---|---|
| 2 | Mineral Trap Assembly |
| 6 | Well |
| 12 | Mineral trap |
| 16 | Housing |
| 20 | Mesh |
| 24 | Mineral trap media |
| 28 | Mineral precipitate |
| 30 | Aquifer |
| 34 | Line |
| 40 | In-situ reactive zone |
| 50 | Screened interval |
| 60 | Pillows |
| 64 | Web |
| 70 | Opening |
| 74 | Perforations |
| 80 | Void |
| 84 | End cap |
| 90 | Sand pack |
| 94 | Pockets |
| 100 | Wall |
| 104 | Inner member |

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

FIGS. 1A-1C are schematics of a mineral trap assembly 2 of one embodiment of the present invention deployed within a standard 2-inch diameter monitoring well 6. The mineral trap assembly 2 is generally comprised of a mineral trap 12 positioned within a housing 16. The mineral trap is further compromised of a fluid-permeable outer member, such as mesh 20, that contains media 24 designed to capture precipitated minerals 28 from groundwater in an aquifer 30. In operation, the mineral trap assembly 2 is held in the aquifer by a line 34. As groundwater infiltrates through mineral trap media 24, mineral grains precipitate solid-phase 28 and/or coatings that are retained. Thus, the mineral trap assembly 2 of one embodiment of the present invention is a passive sampling device for monitoring the formation of reactive minerals in anaerobic in-situ reactive zones (IRZs) 40. The media 24 can be a non-reactive medium (e.g. silica sand), a reactive medium (e.g. iron oxide sand or site soil), or a combination of both. The mineral trap assembly 2 is deployed for a predetermined time in the well 4 at a predetermined depth before, during, or after the implementation of treatment.

A non-reactive medium within the mineral trap provides a carrier substrate upon which target minerals passively form. As a specific example, for application in an anaerobic IRZ setting, geochemically reducing conditions induced during enhanced anaerobic treatment promote the formation of reactive minerals in the mineral trap assembly. Again, reactive media may also be used within the mineral trap assembly to provide a substrate for transformation processes that reflect the natural and/or engineered geochemical conditions within the aquifer. One of ordinary skill in the art will appreciate that mineral trap assemblies can be deployed in other remediation systems and aquifers, not just anaerobic IRZs.

Referring now to FIG. 1C, after predetermined incubation period, the mineral trap assembly 2 is retrieved, preserved, and submitted to a lab for reactive mineral characterization. Dissolved-phase treatment precipitates in the mineral trap assembly and can be examined through minimal sampling time, effort, or cost. More specifically, for both non-reactive and reactive media versions, analysis of the solid phase media within the mineral trap assemblies through chemical, microscopic, or spectroscopic means gives direct evidence of the formation, dissolution, and/or transformation of target minerals in-situ while avoiding the challenges associated with traditional solid-phase sampling techniques. In one embodiment, the reactive materials are characterized using proven analytical methods (USEPA 2009): X-ray Diffraction (XRD), acid volatile sulfide (AVS), chromium extractable sulfide (CrES), and Scanning Electron Microscopy-Energy Dispersive X-ray Spectroscopy (SEM-EDS).

Figure 2:
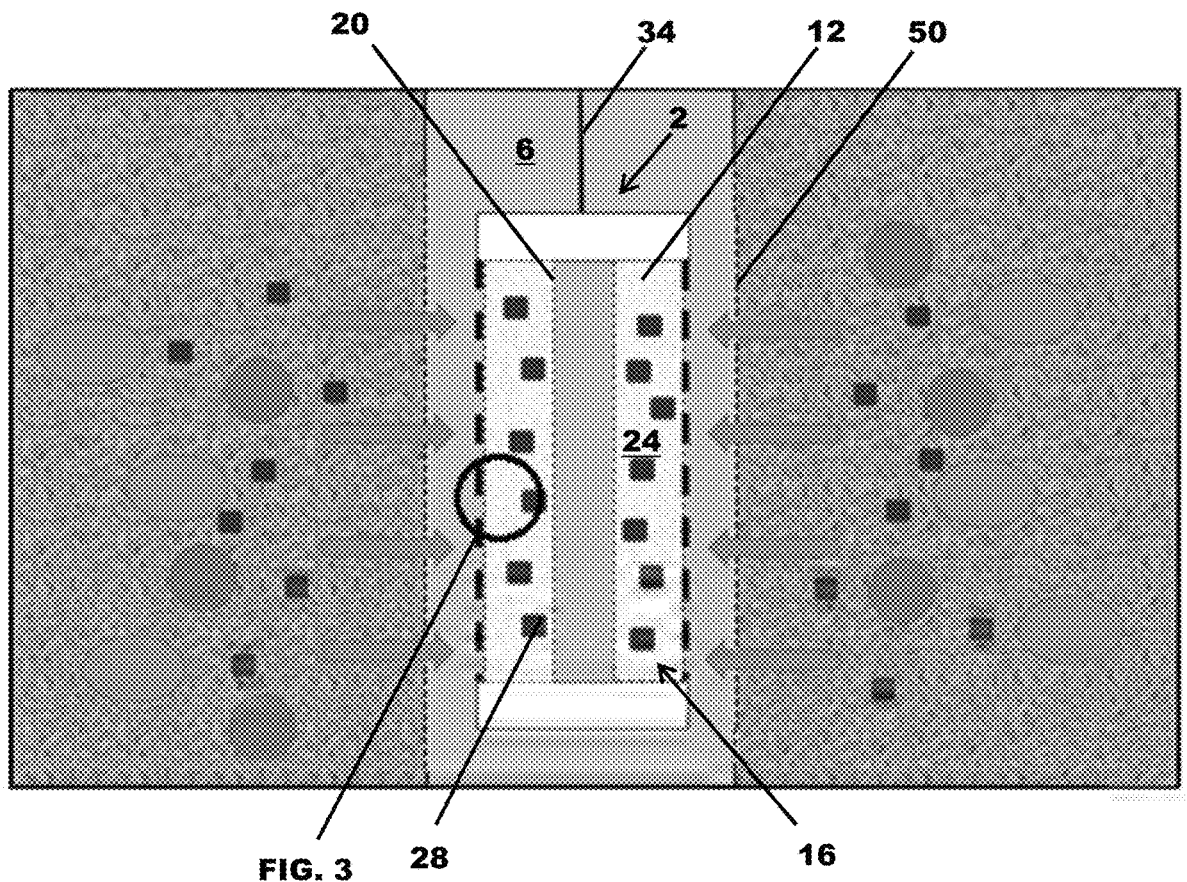
FIG. 2 is a mineral trap assembly of one embodiment of the present invention during an incubation phase.
Figure 3:
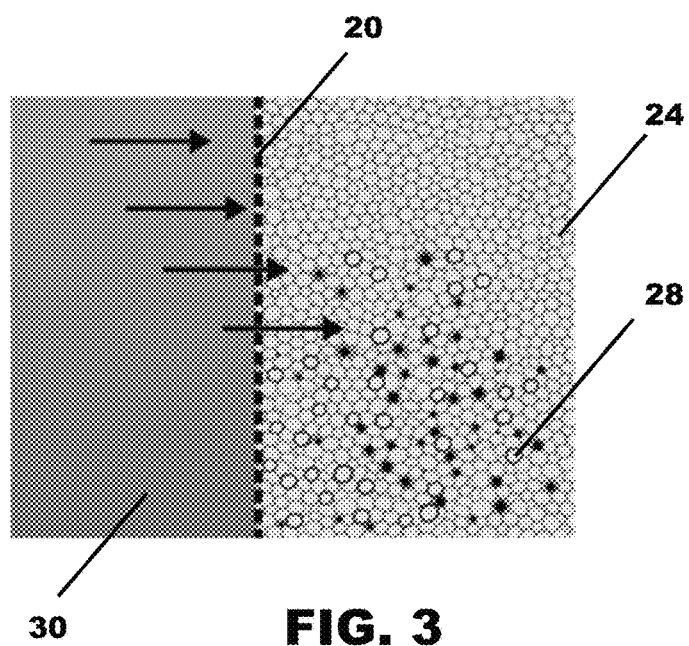
FIG. 3 is a detailed view of FIG. 2 that shows mineral particulate captured within the mineral trap of one embodiment of the present invention.

FIGS. 2 and 3 show the mineral trap assembly 2 of one embodiment of the present invention that directly monitors the formation of minerals associated with a variety of active and passive remediation technologies. As mentioned above, the mineral trap assembly 2 consists of a housing 16 that contains on or more mineral traps 12 comprised of the mineral trap media 24 contained within a water-permeable mesh 20. The media 24 may be solid and porous 10, such as silica sand, iron oxide sand, or site soil. The mineral trap assembly 2 is deployed within a screened interval 50 of a conventional 2-inch (or larger) diameter monitoring well 6 and allowed to incubate for a predetermined amount of time, e.g., 1-3 months. Ambient groundwater flow through the mineral trap assembly's permeable mesh 20 results in the capture of mineral precipitates consistent with processes within the aquifer matrix. In one example, dissolved iron and sulfur combine to form iron sulfide precipitates. Mineral trap assemblies may be deployed as part of an enhanced reductive dechlorination (ERD) remedy in which strong reducing conditions are created through organic carbon injection. The geochemically reducing conditions induced within the in-situ reactive zone (IRZ) promote the formation of reactive iron minerals in the mineral trap. The mineral trap assembly is then retrieved, preserved, and submitted to a laboratory for reactive minerals characterization.

The mineral traps of one embodiment of the present invention were tested in an iron-arsenic co-precipitation experiment simulating aquifer conditions during ISCO with sodium persulfate. The mineral traps successfully captured iron-arsenic precipitates. The relatively fast reaction kinetics of iron-arsenic precipitation (less than 24 hours) resulted in the majority of mineral precipitates 28 forming in the outermost layer (i.e., 2 millimeters) of the mineral trap media 24. More specifically, as FIG. 3 illustrates, depending on the nature of the fluid flow, the characterization of the minerals present in the aquifer and being monitored, and/or the composition of the mineral trap media 24, mineral precipitates 28 may be trapped in such a way to block the internally-situated media, which is often not ideal. Accordingly, one embodiment of the present invention, which will be described in further detail below, employs a unique configuration that maximizes mineral trap surface area to facilitate fluid flow and media exposure so that the majority of the media is exposed to the water being monitored.

Figure 4:
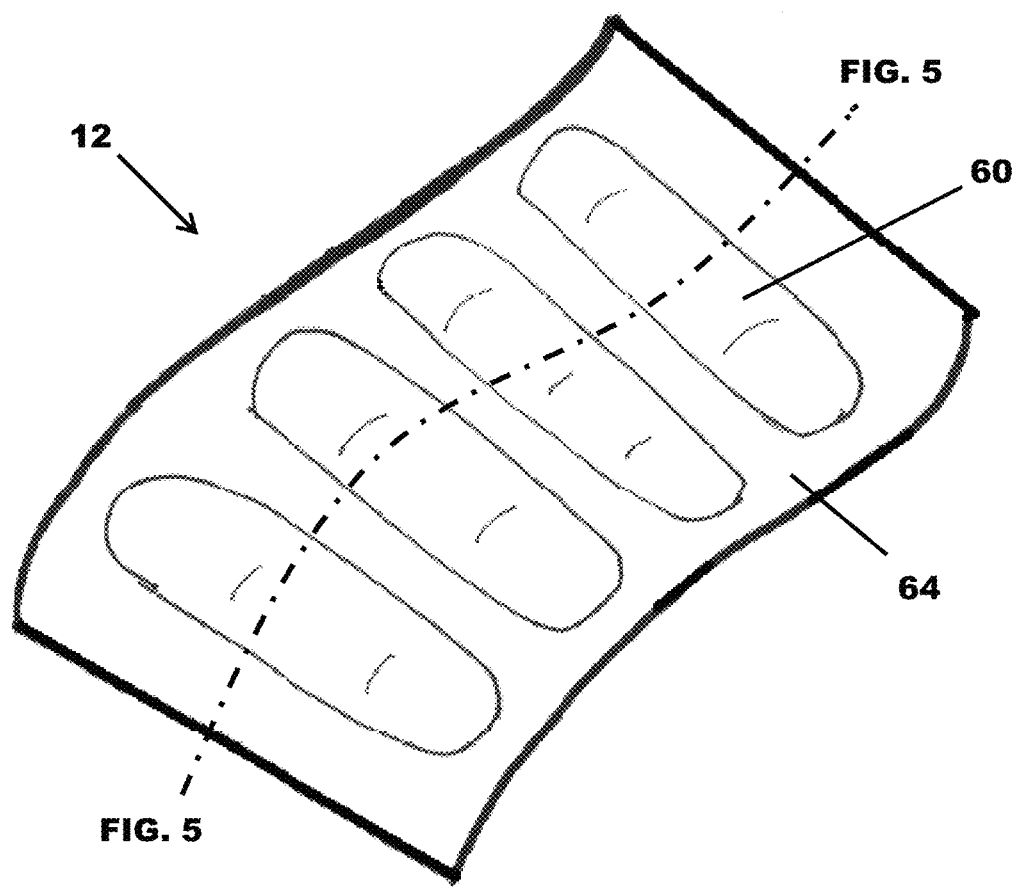
FIG. 4 is a perspective view of a mineral trap employed by some embodiments of the present invention.
Figure 5:
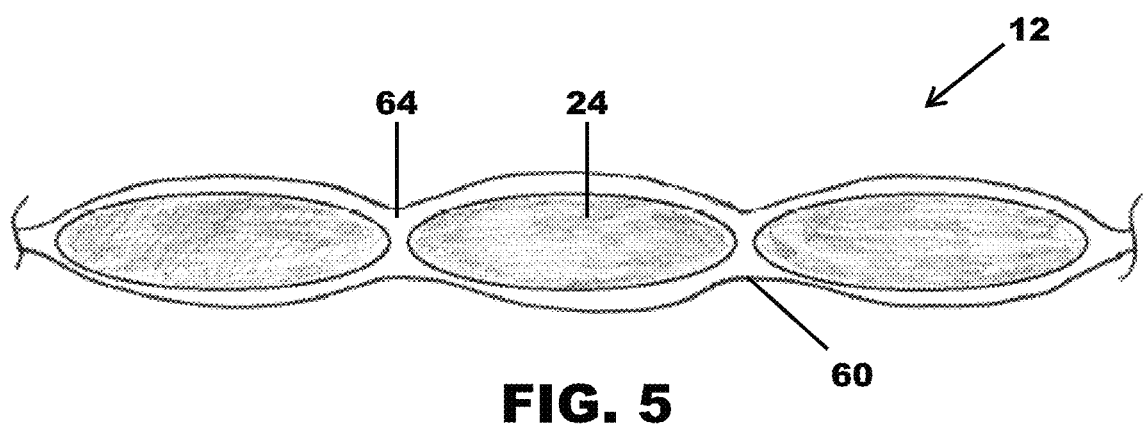
FIG. 5 is a cross-sectional view of FIG. 4.

FIGS. 4 and 5 show a mineral trap 12 of one embodiment of the present invention that has been removed from the housing. A rectangular water-permeable mesh 24 is shown that includes a plurality of elongated pillows 60 that contain the mineral trap media 24. A web 64 is provided between the pillows 60, which allows for the mesh 20 to be selectively curved or bent. This feature allows the mineral trap to be selectively configured to maximize fluid flow and media exposure of the mineral trap assembly.

The initial design of the mineral trap consisted of a vertical strip of parallel pockets of a solid matrix (silica sand). Laboratory testing of this design was conducted in batch reactors without flow, which is representative of an application of mineral traps in an area with very little groundwater movement, or in an area with consistently high solute concentrations, such as within an injection well or a dose-response well located within the injection zone. However, applying the initial mineral trap technology to a system with flow, such as a monitoring well, requires that the flow be concentrated such that it moves through the mineral trap and not around it. Preliminary hydraulic conductivity modeling revealed that by minimizing void space surrounding the mineral trap, the flow through the mineral trap is maximized. Based on this, a cylindrical mineral trap assembly described below was developed.

Figure 6:
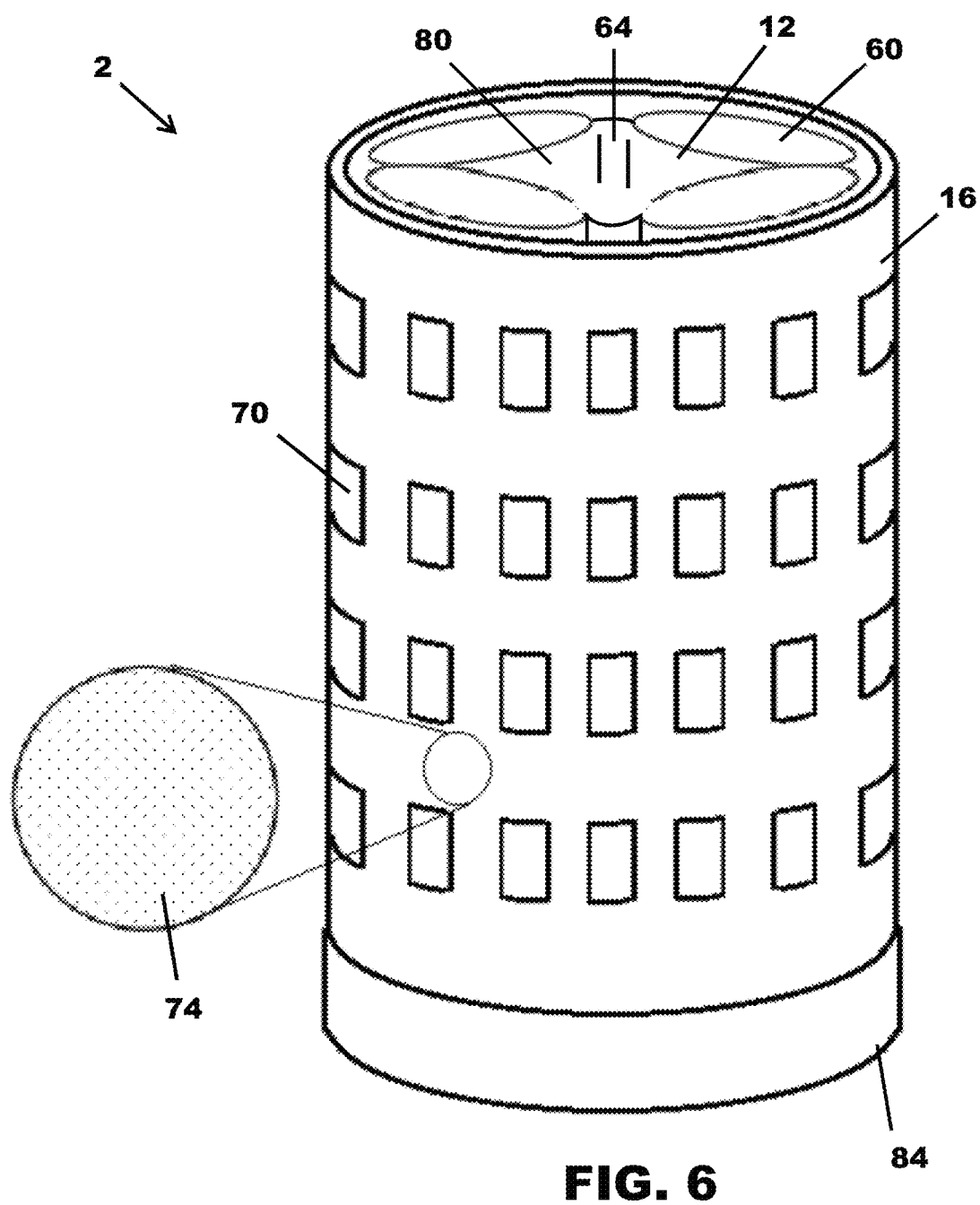
FIG. 6 is a perspective view of a mineral trap assembly of one embodiment of the present invention, wherein a top cap is removed for clarity.

FIG. 6 is a perspective view of the mineral trap assembly of one embodiment of the present invention that comprises the housing 16 that accommodates at least one mineral trap 12. Although the housing 16 shown is cylindrical, one of ordinary skill in the art will appreciate that it can be prismatic, rectangular, or any other shape suited for insertion into a well and an aquifer. The housing 16 also maintains at least one mineral trap 12 in a predetermined orientation. That is, one primary function of the housing 16 is to maintain the orientation of the mineral trap 12 to facilitate fluid flow through the mineral trap assembly 2.

The housing 16 may have a plurality of openings 70 that allow fluid to flow therethrough. In other embodiments, and is shown in the inset, the housing 16 is porous and includes a plurality of small openings 74 that allow fluid to flow therethrough. Openings 70 or pores 74 may be used alone or in combination. Although the Figures may imply the housing 16 is rigid, one of ordinary skill in the art will appreciate that it does not have to be. More specifically, some embodiments the present invention employ a housing 3 comprised of mesh thicker than or similar to that which contains the media. The mineral trap 12 is situated within the housing to provide a void 80 which facilitates fluid flow. The housing may include holding means, such as ledges or clips, which help secure the mineral trap(s) in the desired orientation. In addition, although the mineral trap of FIGS. 4 and 5 is shown positioned in the housing, one of ordinary skill in the art will appreciate that the configuration of the mineral trap is not necessarily critical in some embodiments of the present invention. More specifically, a series of individual mineral traps may be employed that are selectively interconnected to the internal surface of the housing to provide the void 80. An internally-situated cage is provided by some embodiments to maintain the void. End caps 84 that seal an upper portion and a lower portion of the housing 16 may be provided. To facilitate fluid flow, the end caps may include openings or perforations.

Figure 7:
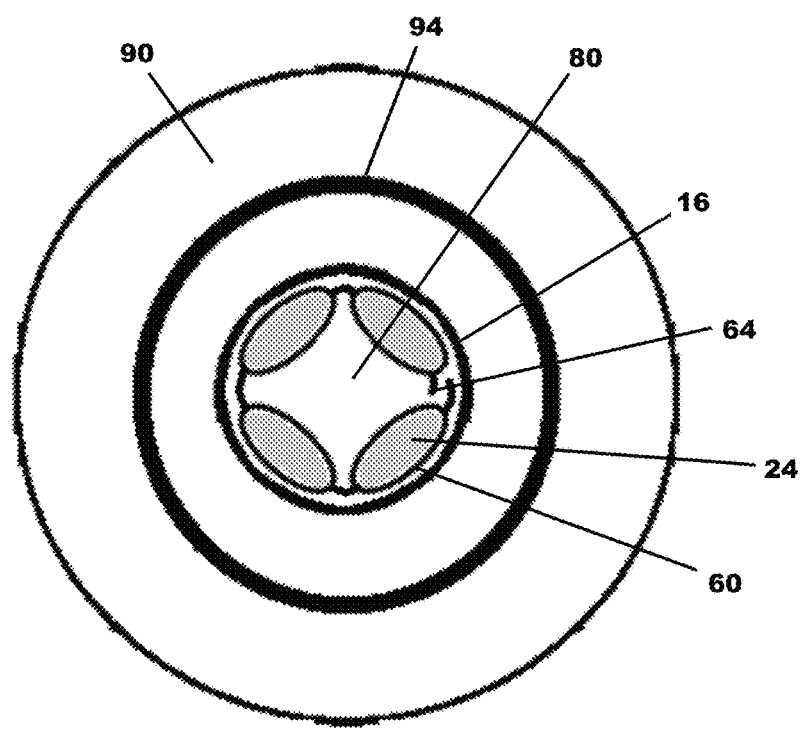
FIG. 7 is a cross-sectional view of FIG. 6.

FIG. 7 is a cross-section of the embodiment shown in FIG. 6, and succinctly shows the void 80. The void 80 is positioned within the ring of pillows 60 that contain the mineral trap media 24. The pillows 60 are interconnected by the webs 64 to define a generally cylindrical mineral trap 12. Fluid flow is, thus, capable flowing through the housing 16 and the mineral trap and expose more of the media to efficiently capture more mineral precipitate.

The design configuration of FIGS. 6 and 7 combines the best features of a mineral trap strip, i.e., high surface area to volume ratio, discrete media pockets that can be cut apart and shipped to different laboratories to be analyzed via various methods, etc., into a system that promotes water and dissolved constituent flux through the mineral trap assembly and not around it. While this may not be a significant concern if mineral traps are being used in high solute mass flux environments, the contemplated system is ideal in low-flux systems where the risk of a false negative result is increased.

Figure 8:
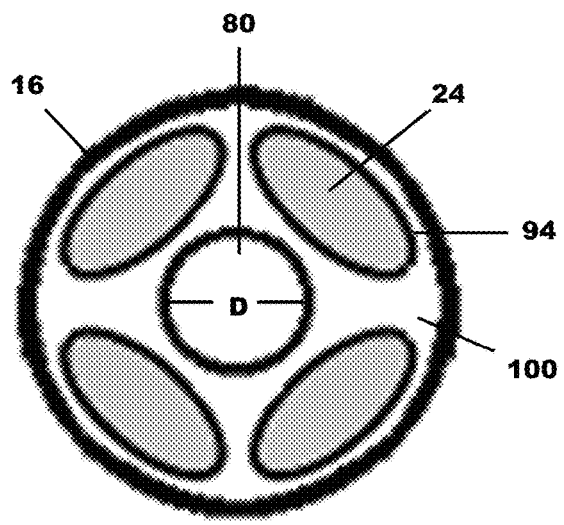
FIG. 8 is a cross-sectional view of FIG. 6 that illustrates an alternative configuration.

FIG. 8 is a cross-section of an alternative embodiment that employs pockets of media 24 and provides a void as in the embodiment shown in FIG. 7. In this version, the housing 16 is made of a fluid-permeable material and pockets 94 are integrated into the housing's side wall 100. The void 80 is provided between the pockets 94. One of ordinary skill in the art will appreciate that the material manufacture of the housing 3 may be rigid, wherein a plastic housing, for example, may be provided that includes a plurality of small openings or pores that emulate mesh and allow fluid flow through the mineral trap assembly. As such, after the mineral trap assembly 2 has incubated for predetermined time it is removed and the contents thereof are placed into a storage vessel for investigation. The housing is then be cleaned and refilled with mineral trap media to be placed into the aquifer.

Figure 9:
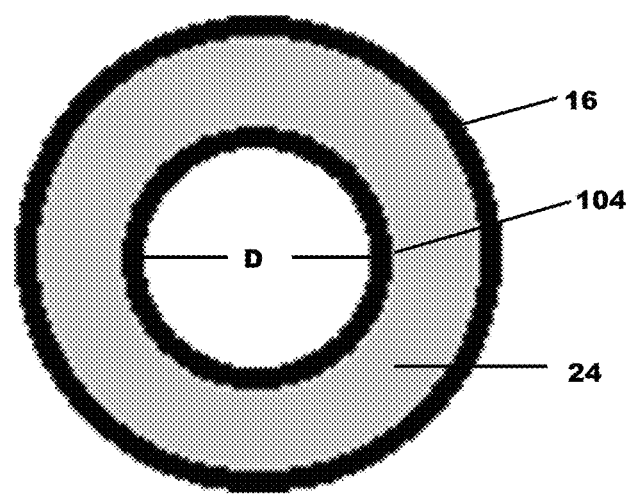
FIG. 9 is a cross-sectional view of FIG. 6 that illustrates an alternate embodiment shown in FIG. 6.

FIG. 9 shows a cross-section of yet another embodiment of the present invention that employs an inner member 104. The media 24 is contained within a volume defined by the inner wall of the housing 16 and an outer wall of the inner member 104. The inner member has a plurality of openings or is porous which allows fluid flow through the mineral trap assembly.

The ability of one embodiment of the mineral trap to capture mineral precipitates was further demonstrated in a laboratory test designed to precipitate iron sulfide minerals. Mineral traps were placed in reaction vessels amended with ferrous sulfate and sodium lactate and inoculated with a culture of sulfate-reducing bacteria (SRB) in a simulated ERD environment. Within 24-hours following inoculation, a black precipitate was observed within the reaction vessels and within the mineral trap's non-reactive sand medium. After approximately 2 days of incubation time, black mineral precipitate was observed throughout the entire thickness of the sand matrix and appeared to be primarily in the form of coatings on sand grains. Laboratory analysis indicated the mineral traps contained more than 400 mg/kg of FeS (as indicated by AVS) and 91/123 mg/kg FeS2 (as indicated by CrES). The table provided below provides some of the data, including Weak Acid Soluble (WAS) iron and Strong Acid Soluble (SAS) iron data.

| Sample | WAS Fe, mg/kg | | | SAS Fe, mg/kg | | | AVS, mg/kg | CrES, mg/kg |
|---|---|---|---|---|---|---|---|---|
| | $Fe^{2+}$ | $Fe^{3+}$ | Total Fe | $Fe^{2+}$ | $Fe^{3+}$ | Total Fe | | |
| 212 μm-0 | 592 | 14 | 607 | 416 | 21 | 437 | 427 | 91 |
| 212 μm-0 dup | 584 | 0 | 584 | 357 | 42 | 399 | 412 | 123 |

Notes:
SAS Fe includes WAS Fe
$Fe^{3+}$ is calculated from the raw data—it is the difference between Total Fe and $Fe^{2+}$.
Discrepancies are due to rounding.

Because sulfate reduction and iron sulfide precipitation are oxygen-sensitive processes, the effect of oxygen exposure on the minerals within the mineral traps during field sampling is a factor. In the laboratory, mineral trap sampling was completed in an anaerobic glove box to document low oxygen exposure conditions and provide reference data for evaluation of real-world field sampling scenarios. The mineral traps were placed in bags with oxygen-scrubbing packets and vacuum sealed within the glove box to minimize exposure to oxygen.

Qualitative testing on the effect of oxygen exposure on iron sulfide minerals was evaluated based on visual sample degradation (i.e., color change from black to red/brown). This approach was designed to simulate a range of field sampling conditions from ideal (30 seconds of air exposure) to the expected maximum amount of time required to preserve samples in a vacuum-sealed bag (15 minutes of air exposure). A reactive iron mineral-bearing mineral trap was cut open and observed. After almost 15-minutes, no indications of degradation were visible, but by 50-minutes, the black color appeared slightly duller and lighter. This transition continued over the almost 3-hour evaluation period. Notably, when the sand grains were turned over, the underlying grains remained black, suggesting that the overlying sand grains provided protection against oxidation within the 3-hour timeframe. If color change is a reliable indicator, these results suggest that the degradation kinetics of iron sulfides in a toxic atmosphere are not rapid enough to damage oxygen-sensitive minerals within fifteen minutes, the maximum expected amount of time for field preservation in a vacuum-sealed bag. This shows that an anaerobic atmosphere is not required for successfully preserving oxygen-sensitive materials in the field. This conclusion would be consistent with laboratory studies stating that XPS results for initial mackinawite and samples exposed to air for 15 minutes to 1 hour are effectively the same.

The minerals captured by the mineral traps of one embodiment may be analyzed with one or more of the following analytical methods:
1. X-ray Diffraction (XRD) for crystalline minerals;
2. Magnetic susceptibility;
3. Scanning Electron Microscopy-Energy Dispersive X-ray Spectroscopy (SEM-EDS) to identify minerals, elemental composition, and crystal morphology and distribution;
4. Total metals concentrations (EPA method 3050B/6010);
5. Sequential selective extractions (SSE) to identify in which mineral phase a constituent is located (e.g., sorbed, carbonate fraction, sulfide fraction, etc.);
6. Leaching studies (e.g., EPA methods 1311/1312);
7. CENSUS® qPCR for Acetylene Hydratase (AHY);
8. Analyses described in the Aqueous and Mineralogical Intrinsic Bioremediation Assessment (AMIBA) protocol (Kennedy et al. 1998):
    Acid volatile sulfide (AVS): the amount of sulfide present as iron monosulfides like mackinawite;
    Chromium extractible sulfide (CrES): the amount of sulfide present as iron disulfides like pyrite;
    Weak acid solution iron (WAS): iron in poorly-crystalline phases; and
    Strong acid solution iron (SAS): iron in crystalline phases.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A device configured to be placed in an aquifer to passively collect particulate matter precipitated from groundwater therefrom, comprising:
    a cylindrical housing having an internal volume defined by a wall, the wall including at least one opening to allow fluid ingress and egress into the internal volume;
    a mineral trap comprised of a fluid-permeable member in the form of a sheet having a plurality of pockets separated by webs positioned between adjacent pockets, the plurality of pockets containing at least one of a reactive or a non-reactive medium;
    wherein the plurality of pockets are positioned adjacent an inner surface of the wall so as to create a void at least partially bound by the mineral trap; and
    wherein the plurality of pockets comprise a first pocket and a second pocket, and wherein a medium in the first pocket is different than a medium in the second pocket.

2. The device of claim 1, wherein the fluid-permeable member is mesh, screen, or a membrane.

3. The device of claim 1, wherein the mineral trap is interconnected to an inner surface of the housing.

4. The device of claim 1, wherein the housing is cylindrical.

5. A method of monitoring water quality, comprising:
    providing a mineral trap assembly, comprising:
        a cylindrical housing having an internal volume defined by a wall, the wall including at least one opening to allow fluid ingress and egress into the internal volume;
        a mineral trap comprised of a fluid-permeable member in the form of a sheet having a plurality of pockets separated by webs positioned between adjacent pockets, the plurality of pockets containing at least one of a reactive or a non-reactive medium; and
        wherein the plurality of pockets are positioned adjacent an inner surface of the wall so as to create a void at least partially bound by the mineral trap;
    inserting the mineral trap assembly into an aquifer;
    removing the mineral trap assembly from the aquifer after a predetermined time;
    removing the mineral trap from the housing;
    severing the fluid-permeable member;
    removing at least a portion of the medium from the fluid-permeable member; and
    analyzing the portion of the medium.

6. The method of claim 5, wherein the fluid-permeable member is first severed along a web to separate adjacent pockets, and wherein the separated pockets are analyzed by separate laboratories.

7. The method of claim 5, wherein, if results of the analysis meet predetermined criteria, an active remediation protocol associated with the aquifer is modified to a passive remediation protocol.

* * * * *